United States Patent
Kasai et al.

[11] Patent Number: 5,886,778
[45] Date of Patent: Mar. 23, 1999

[54] METHOD OF MEASURING ATOMIC BEAM FLUX RATE IN FILM GROWTH APPARATUS

[75] Inventors: Yuji Kasai; Shigeki Sakai, both of Tsukuba, Japan

[73] Assignee: Agency of Industrial Science & Technology, Ministry of International Trade & Industry, Tokyo, Japan

[21] Appl. No.: 959,523

[22] Filed: Oct. 28, 1997

[30] Foreign Application Priority Data

Oct. 28, 1996 [JP] Japan ................................. 8-285054

[51] Int. Cl.⁶ .............................. G01J 3/42; G01N 21/31
[52] U.S. Cl. ............................................. 356/72; 356/311
[58] Field of Search ............................... 356/73, 72, 311, 356/312, 315, 316, 417

[56] References Cited

U.S. PATENT DOCUMENTS 4,911,794  3/1990  Parce et al. ........................... 205/778

OTHER PUBLICATIONS

Komentani et al., J. Vac. Sci. Technol., vol. 12, No. 4, Jul./Aug. 1975, pp. 933–935.
Lu et al., J. Vac. Sci. Technol. A, vol. 13, No. 3, May/Jun. 1995, pp. 1797–1801.
Y. Kasai, et al., "MBE Growth of BiSrCaCuO Films Using Flux Monitoring by Atomic Absorption Spectroscopy", Advances In Superconductivity VII, K. Yamafuji, et al.(Editors), Proceedings of the 7$^{th}$ International Symposium on Superconductivity (ISS'94), Nov. 8–11, 1994, Kitakyushu, Tokyo 1995, pp. 897–900.

M.E. Klausmeier–Brown, et al., "Accurate Measurement Of Atomic Beam Flux By Pseudo–Double–Beam Atomic Absorption Spectroscopy For Growth Of Thin–Film Oxide Superconductors", Applied Physics Letters, vol. 60, No. 5, Feb. 3, 1992, pp. 657–659.

*Primary Examiner*—F. L. Evans
*Attorney, Agent, or Firm*—Oblon, Spivak, McClelland, Maier & Neustadt, P.C.

[57] ABSTRACT

A method of measuring a beam flux rate in a film growth apparatus which includes supplying a hollow cathode lamp with a current that alternates between two current values and does not include a zero current, introducing intensity-modulated spectral light emitted by the hollow cathode lamp into a vacuum chamber of a film growth apparatus, absorbing the light by a beam of atoms projected at a substrate surface, and detecting components synchronized with the modulation of the spectral light obtained.

3 Claims, 5 Drawing Sheets

METHOD OF MEASURING ATOMIC BEAM FLUX RATE IN FILM GROWTH APPARATUS

BACKGROUND OF THE INVENTION

1. Field of the Invention

The present invention relates to a method of using atomic absorption spectroscopy to accurately measure atomic beam flux rate in a vacuum chamber of an apparatus used to grow films, such as a molecular beam epitaxy (MBE) apparatus, a vacuum deposition apparatus, an ion beam deposition apparatus, a laser ablation film fabrication apparatus and a sputter deposition apparatus.

2. Description of the Prior Art

Measurement of atomic beam flux rate in a vacuum chamber of an apparatus used to grow films such as an MBE apparatus, vacuum deposition apparatus, ion beam deposition apparatus, laser ablation film fabrication apparatus, sputter deposition apparatus and the like is important with respect to controlling thin-film fabrication. Atomic absorption spectroscopy (AAS) makes it possible to measure flux rate regardless of the state of the atoms (discrete, molecule or cluster particle, or ionized states thereof). Measurement of beam flux rate in thin-film fabrication apparatuses has been extensively utilized, with a hollow cathode lamp used as the spectral light source.

In a conventional AAS system using a hollow cathode lamp, constant-intensity light emitted by the hollow cathode lamp is interrupted by a mechanical chopper, detected by a photodetector, and the output of the photodetector is locked-in using a lock-in amplifier. Such a system is described, for example, in "MBE Growth of BiSrCaCuO Films Using Flux Monitoring by Atomic Absorption Spectroscopy," by Y. Kasai, A. Suzuki, H. Tanoue, T. Nagai and S. Sakai, (Advances in Superconductivity (vol. 7 (1995) pp. 897–900), and "Accurate measurement of atomic beam flux by pseudo-double-beam atomic absorption spectroscopy for growth of thin-film oxide superconductors," by M. E. Klausmeier-Brown, J. N. Eckstein, I. Bozovic and G. F. Virshup (Applied Physics Letter vol. 60 (1992) pp. 657–659).

However, a problem with the above method in which a mechanical chopper is used is that the magnetic field generated by the motor used to drive the chopper has an adverse effect on observation of the crystal surface using an electron beam, such as in reflection high-energy electron diffraction (RHEED), destabilizing the RHEED image. Another problem is that of vibration produced by the mechanical parts, while a further problem is that the size of the chopper disks imposes constraints on the disposition of the parts making up the optical system, and using a chopper increases the cost of the apparatus.

The object of the present invention is to provide a method of accurately measuring beam flux rate in a vacuum chamber of an apparatus used to grow films, using atomic absorption spectroscopy, without employing a mechanical chopper.

SUMMARY OF THE INVENTION

To attain the above object, the present invention provides a method of measuring beam flux rate in a film growth apparatus, comprising supplying a hollow cathode lamp with a current that alternates between two different current values excluding zero, introducing intensity-modulated spectral light emitted by the hollow cathode lamp into a vacuum chamber of a film growth apparatus and absorbing the light by a beam of atoms projected at a substrate surface, and detecting components synchronized with the modulation of the spectral light obtained.

In the following description, atoms include discrete atoms, molecules and cluster particles, and ionized forms thereof.

In accordance with the present invention, current is supplied to the hollow cathode lamp in pulses. However, if the supply of current to the hollow cathode lamp is intermittent, that is, includes a current value of zero, the result is that the plasma state in the hollow cathode lamp is destabilized, thereby destabilizing the intensity of the light emitted by the lamp. Experiments conducted with the aim of finding preferred operating conditions for the lamp led to the discovery that stable operation could be obtained by using a constant current source to supply the lamp with a current that alternates between two current values.

Since with this arrangement the hollow cathode lamp current never becomes zero, a stable plasma state can be maintained in the hollow cathode lamp, providing stable lamp operation and high-precision intensity-modulation that enables atomic flux rates to be measured with high accuracy. Moreover, since a mechanical chopper is not required, there are no harmful magnetic fields, enabling observation of stable RHEED images. In addition, there is no problem of mechanical vibration, the parts making up the optical system can be arranged with greater flexibility, and the apparatus can be made smaller and produced at lower cost.

Further features of the invention, its nature and various advantages will be more apparent from the accompanying drawings and following detailed description of the invention.

BRIEF DESCRIPTION OF THE DRAWINGS

FIG. 2 (b) is an illustration of the wave form of a current $I_L$ supplied to the hollow cathode lamp.

FIG. 2 (c) is an illustration of a wave form of the intensity $II_L$ of the hollow cathode lamp.

DESCRIPTION OF THE PREFERRED EMBODIMENT

Figure 1:
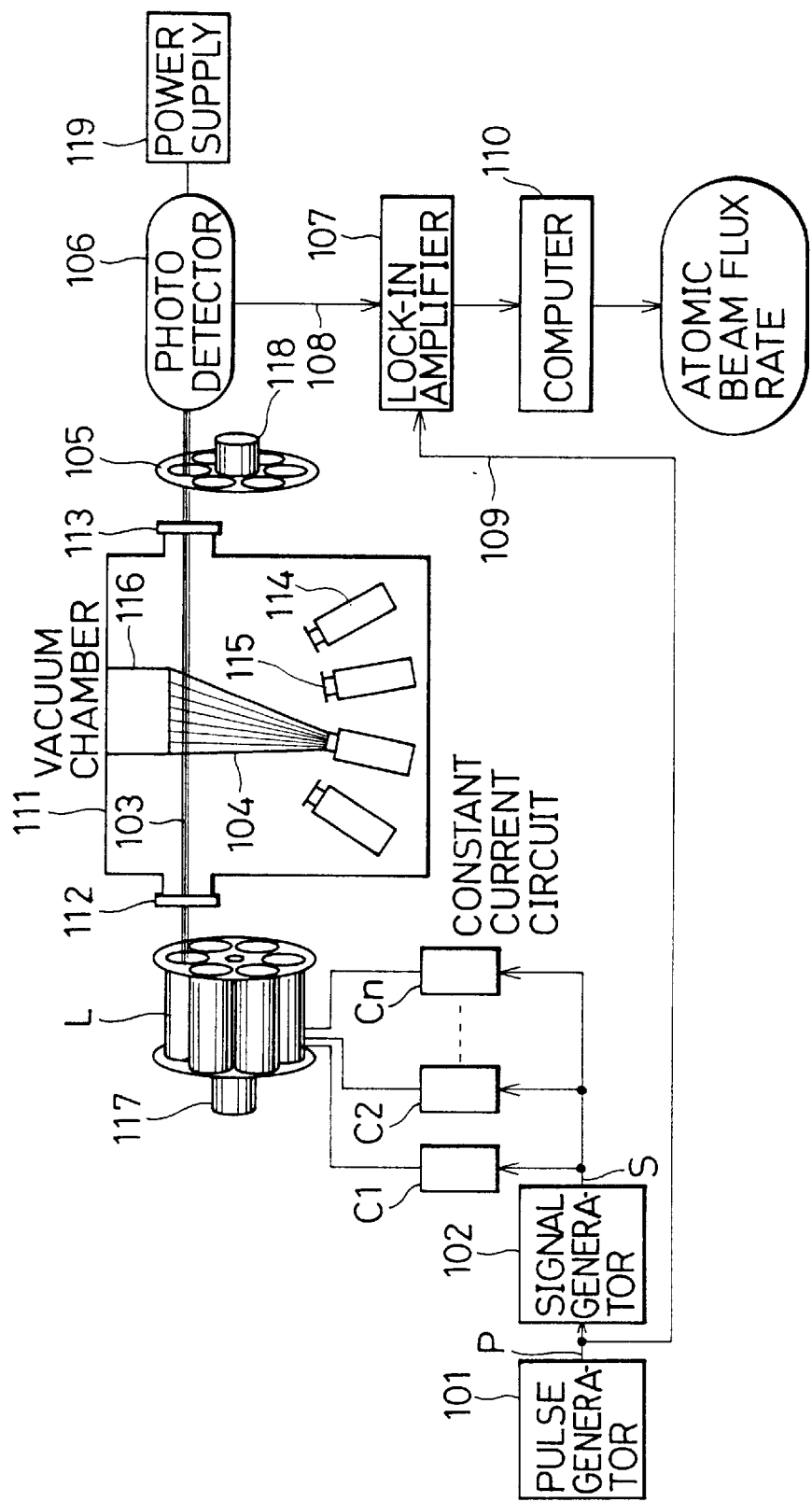
FIG. 1 is a block diagram of an embodiment of an apparatus for implementing the method of measuring beam flux rate in a film growth apparatus according to the present invention.

FIG. 1 illustrates an embodiment of the method of measuring beam flux rate during thin-film fabrication in a vacuum chamber 111, using atomic absorption spectroscopy, in accordance with the present invention. Depiction of RHEED observation devices, evacuation devices and the like has been omitted from FIG. 1. By means of rotating mechanisms 117 and 118, hollow cathode lamps L disposed on one side of the vacuum chamber 111 and line pass filters 105 disposed on the other side of the vacuum chamber 111 can be changed to match the elements to be measured.

A substrate 116 and various flux generators 114 are provided inside the vacuum chamber 111. A film is grown on the surface of the substrate 116 by opening a shutter 115 of a prescribed flux generator 114, whereby the substrate 116 is irradiated by a beam of atoms 104 that are the target of measurement by the present invention. Spectral lines of light 103 emitted by the hollow cathode lamp L and introduced into the vacuum chamber 111 via a viewport 112 are partially absorbed by the atomic beam 104 and pass through viewport 113, are selectively filtered by a line pass filter 105 and detected by a photodetector 106. The photodetector 106 converts the light to an electrical signal 108 that is proportional to the intensity of the received light, and the signal 108 is input to a lock-in amplifier 107. A power supply 119 supplies electrical power to the photodetector 106.

Using the method described below, the intensity of the hollow cathode lamp L is modulated, components synchronized with the modulation are detected by the lock-in amplifier 107, and the atomic flux rate is calculated by a computer 110. Each hollow cathode lamp L is connected to a constant current circuit C1, C2, . . . , Cn. Using output P of a pulse generator 101, signals S comprised of alternations of two different voltage or current values generated by a two-value signal generator 102 are input to the constant-current circuits, causing a set current corresponding to the signal S to be supplied to the hollow cathode lamp L.

Figure 2A:
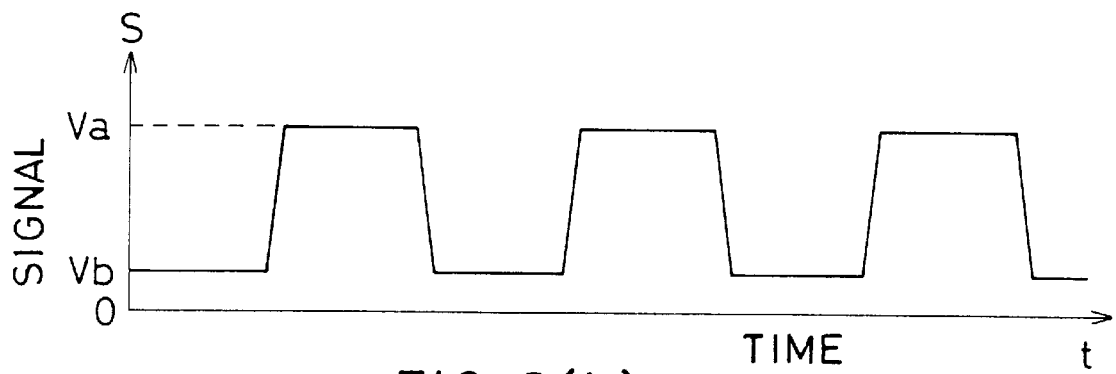
FIG. 2 (a) is an illustration of a wave form of a two-value signal S output by a two-value signal generator.
Figure 2B:
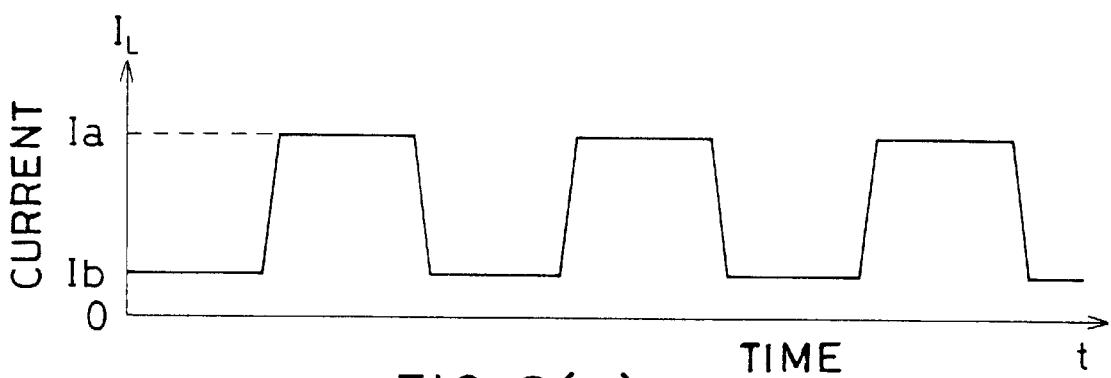
Figure 2C:
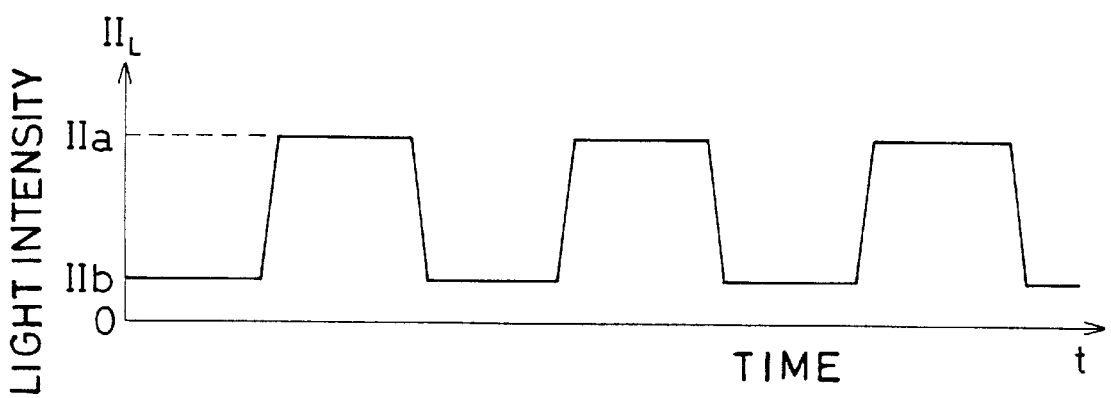

FIG. 2 (a) shows the signal S with two values Va, Vb generated by the two-value signal generator 102. When this signal is input to constant-current circuit C1, C2, . . . , Cn, the hollow cathode lamp is supplied with the current $I_L$ shown in FIG. 2 (b) comprised of repeated alternations of current values Ia, Ib that correspond to the two values of the signal S. If the hollow cathode lamp were to be supplied with a zero-state current, the plasma state in the lamp would become unstable, causing unstable emission intensity. Therefore, the current supplied to the lamp does not go to zero. Based on the current supplied to the hollow cathode lamp, the light emitted by the lamp has an intensity $II_L$ represented by the wave form of FIG. 2 (c). The output P of the pulse generator 101 is sent to the lock-in amplifier 107 as lock-in detection reference signal 109.

Intensities IIa and IIb of the light emitted by the hollow cathode lamp are substantially in proportion to the current values Ia and Ib, and the larger the difference between the intensities, the higher the measurement accuracy. However, the current value Ib cannot be made considerably small because such a small current value destabilizes the plasma state in the hollow cathode lamp. The current value Ib is preferably within the range of 0.03 to 0.3 times the current value Ia.

The frequency of the intensity-modulation of the hollow cathode lamp, namely, the frequency of the output P of the pulse generator 101, is preferably between 50 Hz and 1000 Hz. The two-value signal generator 102 and pulse generator 101 can be integrated by adding an offset to the output of a square wave generator. While a line pass filter 105 is used to select spectral lines, a diffraction grating may be used for the same purpose. Needless to say, the number of hollow cathode lamps used is arbitrary. When only one lamp is used, rotating mechanisms 117 and 118 are not required, and only one constant-current circuit is needed.

The present invention will now be described with reference to an arrangement shown in FIG. 3 in which a lamp operation circuit (two-value signal generator 102 and constant-current circuit C) is used to modulate the intensity of light emitted by hollow cathode lamps L1, L2, . . . , Ln. For this, it is particularly preferable to dispose transistors 302, 303-1, 303-2, . . . , 303-n in a state of thermal contact so that the temperatures of the transistors are uniform. Also, power supply 307 has to be able to produce a voltage that is greater than the discharge initiation voltage of the hollow cathode lamps plus voltage Vb.

Transistor 301 is switched on and off by pulses P output by the pulse generator 101. When transistor 301 is on, the voltage of the two-value signal S is set by constant-voltage diode ZD1, and when transistor 301 is off the voltage of signal S is set by constant-voltage diode ZD2. Taken the relationship between the voltages Vb and Va set by the constant-voltage diodes ZD1 and ZD2 as (Vb<Va), the voltage wave form of signal S is as shown in FIG. 2 (a). The emitter voltage of each of the transistors 303-1, 303-2, . . . , 303-n becomes substantially equal to the signal S voltage, so the respective currents I1, I2, . . . , In of the hollow cathode lamps L1, L2, . . . , Ln, set by resistors R1, R2, . . . , Rn and variable resistors VR1, VR2, . . . , VRn, are proportional to the voltage of signal S. Furthermore, even if there is a change in the hollow cathode lamp voltage, the current value controlled by the signal S voltage is maintained.

It is particularly important that the current to the hollow cathode lamps does not become zero, because the plasma in the hollow cathode lamps has to be maintained in a stable state. Using the above hollow cathode lamp operation circuit, current having the wave form shown by FIG. 2 (b) is supplied to the hollow cathode lamps L1, L2, . . . , Ln, making it possible to achieve with good accuracy the intensity modulation represented by the wave form of FIG. 2 (c). The output of the lock-in amplifier 107 is proportional to the intensity of the intensity-modulated spectral light that has passed through the vacuum chamber 111, so the atomic flux rate can be obtained with good accuracy by measuring said intensity.

Since the method does not need a mechanical chopper, there are no harmful magnetic fields, enabling observation of stable RHEED images. In addition, mechanical vibration is eliminated and the parts making up the optical system can be arranged with greater flexibility, enabling the apparatus to be made more compact. A further merit is that the hollow cathode lamp circuitry used by the method is far cheaper than a mechanical chopper.

Figure 3:
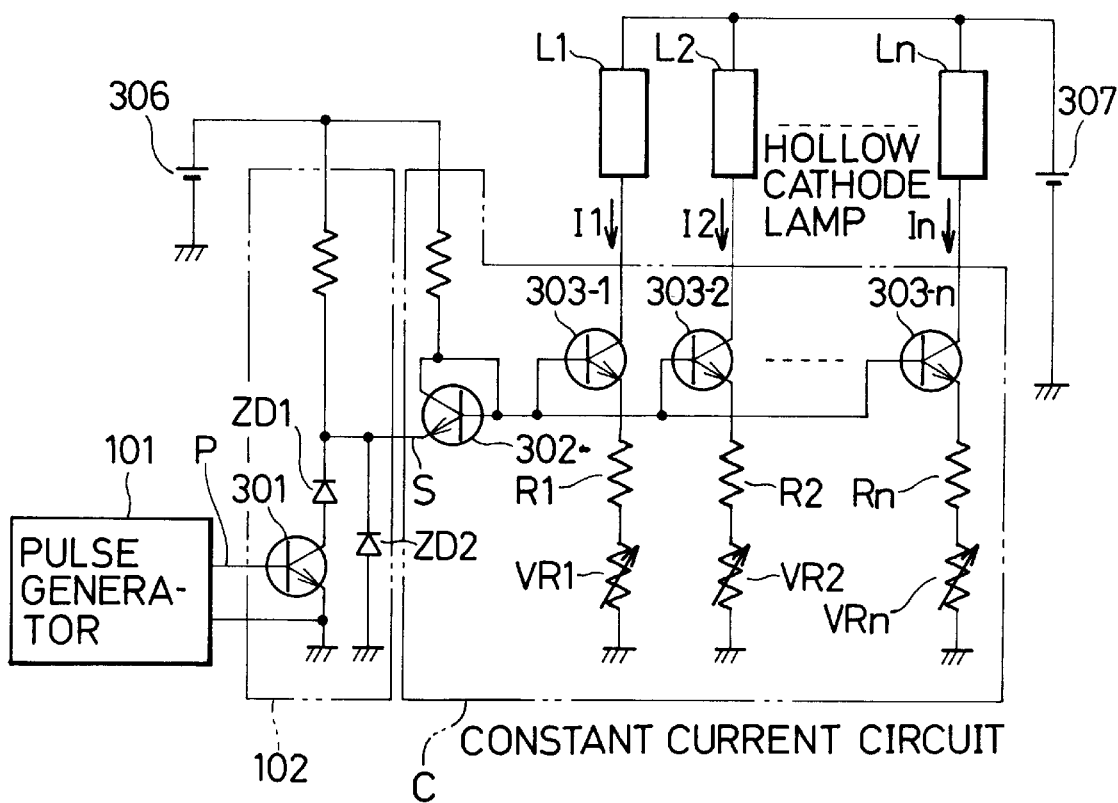
FIG. 3 shows an example of a circuit used to operate the hollow cathode lamp in accordance with the invention.

In FIG. 3, constant-voltage diodes ZD1 and ZD2 are for generating a constant voltage, which may also be achieved by using the forward voltage of light-emitting diodes, the forward voltage of a plurality of ordinary diodes connected in series, an integrated constant-voltage power supply, or the divided output thereof. A normal electronic element having a switching function may be used for the transistor 301.

Figure 4:
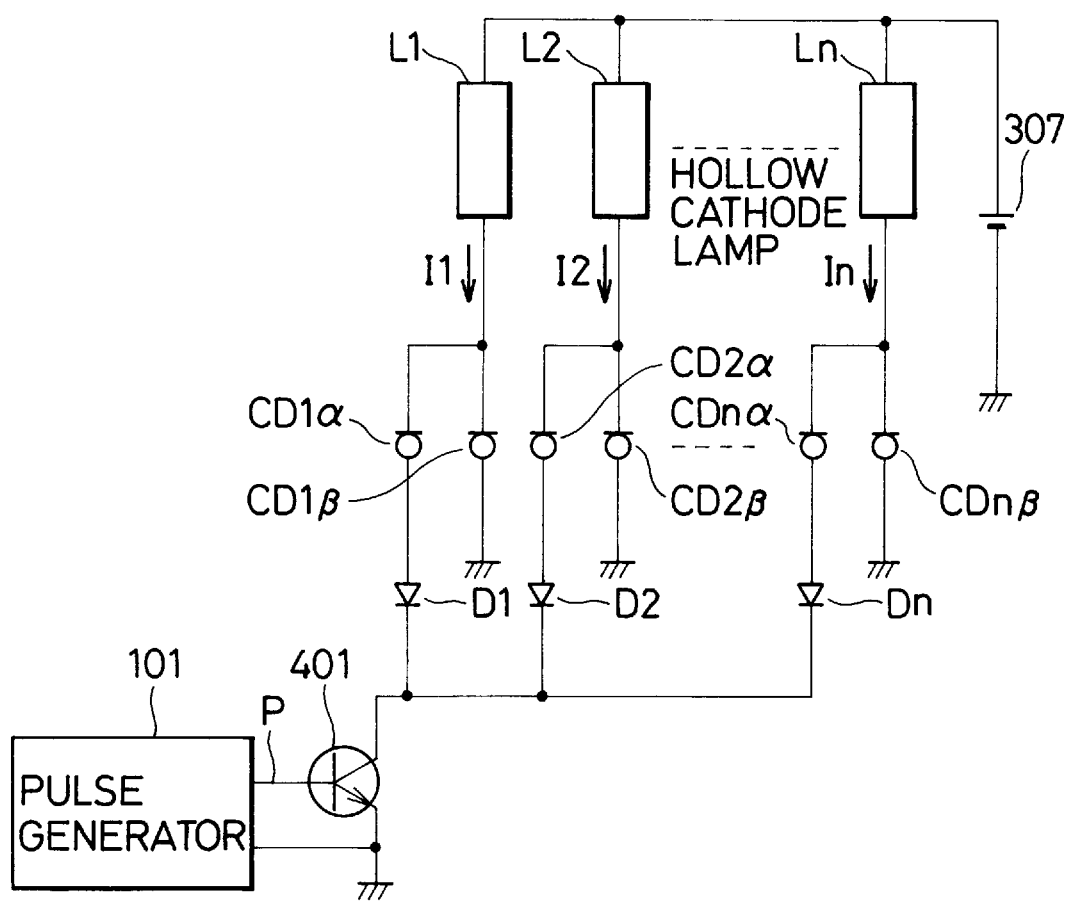
FIG. 4 shows another example of a circuit used to operate the hollow cathode lamp in accordance with the invention.

In the arrangement shown in FIG. 4, constant-current diodes are used instead of the constant-current generator circuit of FIG. 3, which enables the direct generation of two current values. CD1α, CD1β, CD2α, CD2β, . . . , CDnα and CDnβ are constant-current diodes through which flow respective constant currents I1α, I1β, I2α, I2β, . . . , Inα, Inβ.

Focussing just on hollow cathode lamp L1, when transistor 401 is on, lamp current I1 is the sum of I1α and I1β, and when transistor 401 is off, lamp current I1 is I1β. The same applies to hollow cathode lamps L2, . . . , Ln. In the arrangement of FIG. 4, the signal S output by the two-value signal generator is current output, and this signal S is used to directly operate the hollow cathode lamp. The wave form obtained is the same as that obtained with the circuit arrangement of FIG. 3, and as well as providing the same effect as the FIG. 3 arrangement, is an extremely simple circuit configuration.

Figure 5:
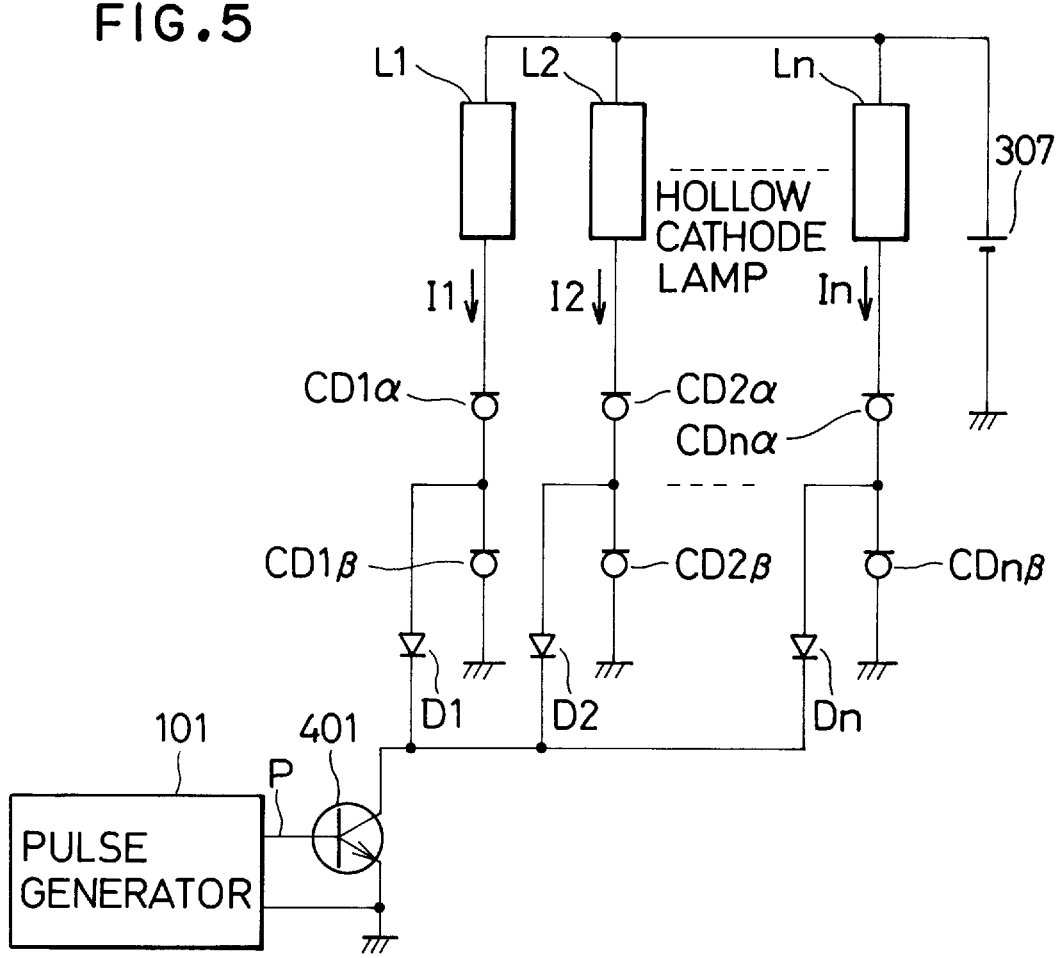
FIG. 5 shows a further example of a circuit used to operate the hollow cathode lamp in accordance with the invention.
Figure 6:
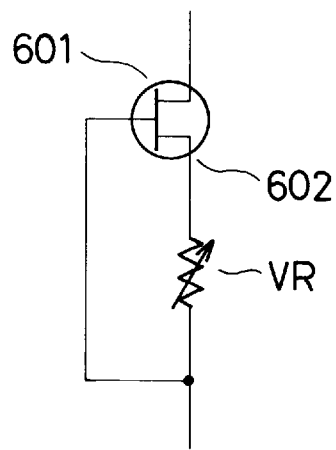
FIG. 6 shows an example of a circuit used in place of the constant current diode used in the arrangements of FIG. 4 and FIG. 5.

While in FIG. 4 the constant-current diodes are connected in parallel, they may instead be connected in series, as shown in FIG. 5, and a switching circuit is provided in parallel with the diode having a smaller rated current. The constant-current diodes of FIGS. 4 and 5 may be replaced by the circuit arrangement shown in FIG. 6, comprising a variable resistor VR connected to source electrode 602 of a depression type field-effect transistor 601. This has the advantage of enabling the lamp current setting to be changed by means of the variable resistor VR.

In accordance with this invention, stable observation of RHEED images is possible because a mechanical chopper is not required, which also eliminates problems caused by vibration, the parts making up the optical system can be arranged with greater flexibility, and the apparatus can be made smaller and produced at lower cost.

Obviously, numerous modifications and variations of the present invention are possible in light of the above teachings. It is therefore to be understood that within the scope of the appended claims, the invention may be practiced otherwise than as specifically described herein.

What is claimed is:

1. A method of measuring a beam flux rate in a vacuum chamber of a film growth apparatus in which a beam of atoms is projected at a substrate surface, comprising;

supplying a hollow cathode lamp with a current that alternates between two different constant current values excluding zero so that the hollow cathode lamp emits into said vacuum chamber intensity-modulated spectral light, which is partially absorbed by the beam of atoms projected at said substrate surface; and detecting components of the intensity-modulated light transmitted through the beam of atoms projected at the substrate surface in synchronization with the modulation of the intensity-modulated spectral light.

2. The method according to claim 1, wherein one of the two current values is within a range of 0.03 to 0.3 times the other of the two current values.

3. A method according to claim 1, wherein a frequency of the modulation of the intensity-modulated spectral light is within a range of 50 Hz to 1000 Hz.

* * * * *